United States Patent [19]

Thien

[11] Patent Number: 4,710,570
[45] Date of Patent: Dec. 1, 1987

[54] AZINE REDOX DYES AND LEUCO AZINE DYES

[75] Inventor: Tran V. Thien, Harlow, United Kingdom

[73] Assignee: Minnesota Mining and Manufacturing Company, St. Paul, Minn.

[21] Appl. No.: 781,913

[22] Filed: Sep. 30, 1985

[51] Int. Cl.$^4$ .................. C07D 265/38; C07D 279/20
[52] U.S. Cl. ........................ 544/31; 544/34; 544/35; 544/99; 544/101; 544/102; 544/104
[58] Field of Search .................. 544/31, 34, 35, 99, 544/101, 102, 104

[56] References Cited

U.S. PATENT DOCUMENTS 3,697,590 10/1972 Boisser et al. ............ 544/35 X
3,803,140 4/1974 Cook et al. ............... 544/35

FOREIGN PATENT DOCUMENTS 1516746 2/1968 France .
1496790 1/1978 United Kingdom .

Primary Examiner—Richard L. Raymond
Attorney, Agent, or Firm—Donald M. Sell; James A. Smith; Mark A. Litman

[57] ABSTRACT

Azine redox dyes and their corresponding dyes of the formula:

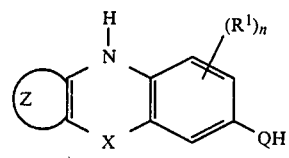

or

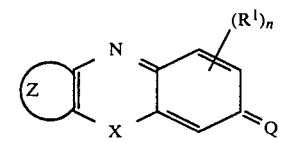

in which:
X is O, S, $NR^2$,
Z completes a fused aromatic of heterocyclic ring system,
n is 0 or 1 to allow one $R^1$ ring substituent,
Q represents $CR^4R^5$ in which at least one of $R^4$ and $R^5$ is an electronegative group or $R^4$ and $R^5$ may complete a ring, or
when X is S Q may represent $NR^3$ in which $R^3$ is an aromatic or heterocyclic group.

The leuco dyes are useful as dye generators in pressure sensitive, thermographic or photothermographic imaging systems.

12 Claims, No Drawings

AZINE REDOX DYES AND LEUCO AZINE DYES

FIELD OF THE INVENTION

This invention relates to novel azine redox dyes and to their corresponding leuco dyes. In particular, the invention relates to a group of leuco azine dyes which are suitable as dye-forming agents in pressure-sensitive, thermographic, photothermographic and photographic imaging systems.

BACKGROUND OF THE INVENTION

In contrast to cationic redox dyes such as methylene blue, and xanthene dyes which undergo one electron redox reaction, leuco azine dyes of the present invention undergo a two electron redox reaction involving a quinonoid form, the azine dye form.

The preparation of certain azine dyes by oxidative coupling of phenothiazine or phenoxazine with carbon or nitrogen nucleophiles has been described by, inter alia, F. Kehram (Ann. Chem. 1902, 322, 1, 45) J. A. Van Allan et al (J. Org. Chem. 1969, 34, (6), 1691) and J. Daneke (Ann. Chem. 1970, 740, 52).

We have discovered a range of new azine dyes, and their corresponding leuco or-reduced forms, which are useful in various imaging systems.

SUMMARY OF THE INVENTION

According to the present invention, there is provided a compound of the general formula:

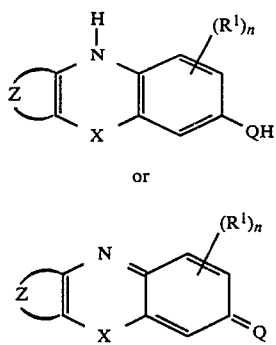

in which:
X represents O, S or $NR^2$, where $R^2$ is an alkyl group of 1 to 4 carbon atoms;
Z represents the necessary atoms to complete a fused aromatic or heterocyclic ring system, which may be polynuclear, of up to 16 skeletal atoms selected from carbon and nitrogen, preferably the ring completed by Z contains 5 or 6 skeletal atoms;
n is 0 or 1;
$R^1$ contains up to 15 skeletal atoms selected from carbon, nitrogen, oxygen, sulphur and halogen, and represents an optionally substituted aliphatic, aromatic, carboxy, amino, alkoxy, aryloxy or sulphonyl group, or halogen, preferably $R^1$ represents an optionally substituted aromatic or alkyl sulphonyl group, more preferably a phenyl sulphonyl group;
Q represents $CR^4R^5$
in which
$R^4$ and $R^5$ contain up to 20 skeletal atoms selected from carbon, nitrogen, oxygen and sulphur, at least one of $R^4$ and $R^5$ is an electronegative group selected from optionally substituted carbonyl, cyano and sulphonyl groups, and substituted aryl groups, and the other of $R^4$ and $R^5$ may additionally be selected from aryl, alkoxy, thioalkoxy, alkylamino and arylamino, or $R^4$ and $R^5$ together comprise the necessary atoms to form a 5-membered α-oxoheterocyclic ring, and when X represents O or $NR^2$, $R^4$ and $R^5$ together may additionally comprise the necessary atoms to form a 6-membered α-oxoheterocyclic ring, and when X is $NR_2$, Q may additionally represent $NR^3$
in which
$R^3$ contains up to 15 skeletal atoms selected from carbon, nitrogen, oxygen and sulphur and represents an optionally substituted aromatic or heterocyclic ring system, which may be polynuclear.
Where X is $NR^2$, preferably $R^2$ is methyl.
Z generally represents a fused phenyl ring or pyridine ring, which may be substituted, e.g. by a perfluoroalkyl group such as $CF_3$.
$R^1$ may be from alkyl, alkoxy, aryl, aryloxy, amino, alkylamino, dialkylamino, arylamino, diarylamino, carboxy, carboalkoxy, cyano, carbamido, halogen, optionally substituted arylsulphonyl, heterocyclic-substituted sulphonyl and alkylsulphonyl (optionally perfluorinated). It is most preferred that $R^1$ represents optionally substituted arylsulphonyl or perfluoroalkylsulphonyl groups. A substitutent on an arylsulphonyl group will generally be selected from alkyl, alkoxy, halogen, nitro, and a further fused ring.

Compounds of the invention in which $R^1$ is a sulphonyl group may be prepared according to the following reaction scheme:

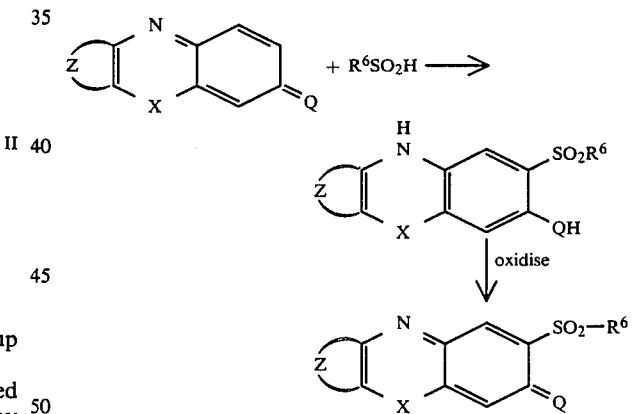

in which $R^6$ represents any of the sulphonyl substituents mentioned above.

The sulphinic acid $R^6SO_2H$ is obtained from its sodium salt which is in turn prepared according to the following reaction scheme

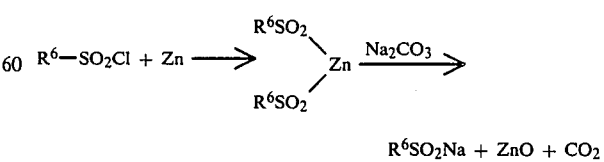

$R^6SO_2Na + ZnO + CO_2$

The sulphonyl chloride is obtained from the sulphonic acid which has been generated by acidification of the corresponding sodium salt with hydrochloric acid.

Examples of suitable $R^3$ groups, when Q is $-NR^3$, include aryl, substituted aryl such as alkaryl, alkenylaryl, arylalkenylaryl, hydroxyaryl, hydroxyalkylaryl, alkoxyaryl, aryloxyaryl, aminoaryl, carboxyaryl, carboalkoxyaryl, carbamidoaryl, cyanoaryl, sulphoxyaryl, and halogenoaryl; heterocyclic rings such as pyridyl, quinolyl, thiazolyl, benzothiazolyl, benzoxazolyl, benzimidazolyl, thiadiazolyl, and oxadiazolyl.

Suitable electronegative groups for $R^4$ and $R^5$ include carboxy, carboalkoxy, carboaryloxy, carbamido, arylaminocarbonyl, cyano, alkylsulphonyl (including perfluorinated alkylsulphonyl), arylsulphonyl, sulphamido, nitroaryl, cyanoaryl, alkanoyl, and aroyl.

$R^4$ and $R^5$ together may form an α-oxoheterocyclic ring such as oxazolidinone, thioxo oxazolidone, thiazolidone, thioxothiazolidone, oxazolone, thiazolone, pyrazolone, isoxazolone, isothiazolone, oxoisocoumarin, diazolidinedione, indanone, 1,3-dioxane-4,6-dione, which may be substituted by alkyl, aryl or fused ring groups.

Azine dyes of formula II in which Q is $NR^3$ can be prepared by oxidative coupling of the corresponding azine, such as phenothiazine or phenoxazine, with a suitable compound, such as a substituted aniline or a heterocyclic amine, in the presence of an oxidising agent such as iodine, bromine or ferric chloride, and preferably under neutral or alkaline conditions below 40° C.

Azine dyes of Formula II in which Q is $CR^4R^5$ can be conveniently prepared by oxidative coupling of the corresponding azines with a suitable carbanion formed in situ, e.g. from ketomethylene compounds, in the presence of potassium acetate and an oxidiser such as iodine. The reaction is preferably carried out below 40° C.

Beside displaying a wide range of absorptions from orange to near infrared, most redox azine dyes of this invention possess relatively high redox potential that makes them easily reducible to the colourless leuco form.

The leuco dyes of the present invention are useful in pressure-sensitive, thermographic, photothermographic and photographic imaging systems.

Photothermographic materials often referred to as "dry silver" or "thermally processed silver" systems were originally introduced in the 1960's for electron beam recording of computer output data and for retrieving prints from various forms of microfilm. The ease of handling of these materials, and the absence of wet processing has encouraged their acceptance as convenient rapid-access information storage and retrieval media. More recently dry silver has evolved into other fields including electro-optic imaging and continuous tone duplication.

In the basic dry silver process light striking the coated surface of a dry silver medium forms a stable latent image. This latent image catalyses the formation of silver metal upon heating, i.e. a silver image is formed.

The material that forms the light sensitive part of dry silver media is silver halide, and responds to light in much the same manner as in wet silver halide systems. The essential elements for a dry silver system are: (1) a silver halide latent image forming material in catalytic proximity to a light stable, heat reducible silver compound, and (2) stable chemicals that will reduce silver compounds during heating. Light energy is used to produce the catalyst and heat energy is used to produce the silver image.

Most commonly one finds two layers on a suitable substrate comprising an imaging layer and a topcoat, although some elements may additionally include prime layers, barrier layers and backside layers. The substrate may be either transparent or opaque and, therefore, either film or paper (both treated and untreated) can be used. The light sensitive imaging layer contains silver halide(s) in reactive association with a light insensitive silver salt, commonly the silver salt of a fatty acid, such as silver behenate and may also contains such developers, resins, toners, sensitising dyes, etc., as necessary to adapt the construction to its intended purpose. The topcoat is, most commonly, a barrier layer although in some constructions it contains reactive ingredients. Considerations associated with emulsion pot-life and coatability dictate the composition of each layer.

Because all the processing chemistry resides in the construction, heating an exposed element develops the latent image in a diffusion-controlled process. Processing conditions for current products range from 3 to 60 seconds at 120° to 140° C. Current film constructions require 15 to 20 seconds at 130° C., while paper constructions develop more quickly at slightly lower temperatures. The most common form of processing an exposed element is to pass the material over a precisely-controlled, heated drum. However, the use of hot air, or heat produced "in-situ" using a conductive backside coating is also known.

Spectral sensitisation of dry silver materials is analogous to conventional silver halide materials in that the common sensitiser families such as cyanines and merocyanines are quite effective. The environment around the silver halide in dry silver materials requires that cyanine sensitisers contain a highly polar group such as an acid function or its salt for maximum efficiency. Proper selection of spectral sensitisers has allowed the sensitisation of dry silver materials to all regions of the visible spectrum and to the near infrared, allowing their use with a variety of cathode ray tube phosphors ranging from blue to red and a variety of light sources including broad, intermediate and narrow emission sources. Laser diode sources emitting in the infrared or visible region of the spectrum may also be used.

Although traditional dry silver formulations give an image composed entirely of silver, the basic systems can be modified by the addition of dye forming materials. These can either give coloured images or increase the image density without an increase, or even while decreasing the silver content of the emulsion layer.

U.S. Pat. No. 4,021,240 discloses the use of sulphonamidophenol reducing agents and four equivalent photographic colour couplers in thermographic and photothermographic emulsions to produce dye images including multicolour images.

U.S. Pat. No. 4,022,617 discloses the use of leuco dyes (referred to as leuco base dyes) in photothermographic emulsions. These leuco dyes are oxidised to form a colour image during the heat development of the photothermographic element. A number of useful toners and development modifiers are also disclosed.

Research Disclosure 17029, "Photothermographic Silver Halide Systems", pp. 9–15, discloses photothermographic systems and discusses attempts to provide colour to them. The above referenced patents and other art, e.g. U.S. Pat. Nos. 4,022,617, 3,180,731 and 3,761,270, are noted as relevant to the subject of providing dye density and colour images to photothermographic emulsions.

The leuco dyes of the present invention are suitable for use in dry silver systems generating a colour image upon heat development. Particularly useful dyes have an oxidation potential within the range 0.2 to 0.7 volts.

Traditionally copies of writing by pressure sensitive imaging techniques were produced solely by inserting a sheet of carbon or coping paper between the original and the intended copy. The impression was obtained through the transfer of carbon, by virtue of the writing pressure, from the layer on the carbon paper onto the sheet underneath. This technique is simple, but has certain drawbacks. Parts of the assembly readily shift out of register and the whole composite is therefore difficult to manipulate. The carbon paper tends to soil both the fingers and the copy. These adverse factors prompted a search for an improved, "cleaner" method of copying which has lead to the development of an alternative pressure sensitive imaging system known as carbonless copy paper (C.C.P).

In the simplest form of this system a top sheet, which has on its underside a coating of microcapsules which contain a solution of a colourless dye precursor or colour former in a solvent, is placed in contact with a bottom sheet which has, on its frontside, a coating of a reagent, referred to as the coreactant, which can react with the colour former to generate a dye. Pressure on the top sheet, exerted in the writing process, ruptures the microcapsules and the solution which they contain is transferred into reactive association with the coreactant. The ensuing reaction generates the dyestuff to form the desired image. Multiple copies can be formed by placing sheets which have a frontside coating of coreactant and a backside coating of colour forming microcapsules between the above described top and bottom sheets. One embodiment of this system utilises a topsheet coated with micro-encapsulated benzoyl peroxide and a bottom sheet coated with a leuco dye which can be oxidised to generate a dye when the peroxide microcapsules are ruptured. The leuco dyes of the present invention may readily be utilised in such copying systems.

The following Table 1 reports the characteristics of azine dyes of Formula (II). The absorption wavelengths were measured in dichloromethane.

TABLE 1

| No. | DYE | $\lambda_{max}$ (nm) | Yield |
|---|---|---|---|
| AD-1 | [structure] | 548 | 50% |
| AD-2 | [structure] | 525 | 45% |
| AD-3 | [structure] | 590 | 42% |
| AD-4 | [structure] | 576 | 39% |
| AD-5 | [structure] | 570 | 30% |
| AD-6 | [structure] | 590 | 26% |

TABLE 1-continued

| No. | DYE | $\lambda_{max}$ (nm) | Yield |
|---|---|---|---|
| AD-7 | (phenothiazine)=C(CN)(SO$_2$Me) | 577 | 19% |
| AD-8 | (phenothiazine)=C(COPh)(COPh) | 532 | 40% |
| AD-9 | (phenothiazine)=C(SO$_2$CF$_3$)$_2$ | 646 | 65% |
| AD-10 | (phenothiazine)=C(CN)(2-CN-C$_6$H$_4$) | 542 | 36% |
| AD-11 | (phenothiazine)=(3-phenyl-isoxazol-5(4H)-one-4-ylidene) | 640 | 28% |
| AD-12 | (phenothiazine)=C(CO$_2$Et)(COPh) | 550 | 40% |
| AD-13 | (phenothiazine)=C(CN)(4-NO$_2$-C$_6$H$_4$) | 555 | 35% |
| AD-14 | (phenothiazine)=N-C$_6$H$_4$-CO$_2$Et | 510 | 76% |
| AD-15 | (phenothiazine)=N-C$_6$H$_4$-Cl | 508 | 85% |

TABLE 1-continued

| No. | DYE | λ$_{max}$ (nm) | Yield |
|---|---|---|---|
| AD-16 | phenothiazine=N-C$_6$H$_4$-I | 510 | 30% |
| AD-17 | phenothiazine=N-C$_6$H$_4$-NHCOCH$_3$ | 522 | 77% |
| AD-18 | phenothiazine=N-C$_6$H$_4$-CH$_3$ | 512 | 60% |
| AD-19 | phenothiazine=N-C$_6$H$_4$-OCH$_3$ | 530 | 71% |
| AD-20 | phenothiazine=N-C$_6$H$_3$(OCH$_3$)$_2$ | 550 | 49% |
| AD-21 | phenothiazine=N-C$_6$H$_4$-NEt$_2$ | 640 | 63% |
| AD-22 | phenothiazine=N-C$_6$H$_4$-N(Et)(CH$_2$CH$_2$OH) | 640 | 50% |
| AD-23 | phenothiazine=N-C$_6$H$_4$-CH(OH)CH$_3$ | 506 | 60% |
| AD-24 | pyrido-thiazine=N-C$_6$H$_4$-CO$_2$Et | 495 | 28% |

TABLE 1-continued

| No. | DYE | λ$_{max}$ (nm) | Yield |
|---|---|---|---|
| AD-25 | [structure: phenothiazine-quinone imine with N-(2-methyl-4-diethylaminophenyl)] | 670 | — |
| AD-26 | [structure: phenothiazine-quinone imine with thiazoline-Me substituent] | 663 | — |
| AD-27 | [structure: phenothiazine-quinone imine with benzothiazolyl substituent] | 662 | — |
| AD-28 | [structure: 4-(trifluoromethyl)phenothiazine quinone with dicyanomethylene] | 562 | 18% |
| AD-29 | [structure: N-methyl phenazine quinone with dicyanomethylene] | 675 | 15% |

The following Table 2 reports some leuco azine dyes of Formula 1 found useful in the practice of the invention. Where available halfwave oxidation potentials ($E_{ox}$) (in volts relative to a silver/silver chloride electrode) are reported.

TABLE 2

| No. | Leuco Dye | $E_{ox}$ |
|---|---|---|
| LAD-1 | [structure: phenothiazine-NH with CH(CO$_2$Et)$_2$ substituent] | |
| LAD-2 | [structure: phenothiazine-NH with CH(COPh)(CO$_2$Et) substituent] | |
| LAD-3 | [structure: phenothiazine-NH with CH(SO$_2$CF$_3$)$_2$ substituent] | |

TABLE 2-continued

| No. | Leuco Dye | $E_{ox}$ |
|---|---|---|
| LAD-4 | phenothiazine-NH-Ph-CH(COPh)(COPh) | |
| LAD-5 | phenothiazine-NH-Ph(SO₂Ph)-CH(COPh)(COPh) | |
| LAD-6 | phenothiazine-NH-Ph-CH(Ph)(CN), with o-CN on phenyl | +0.30 |
| LAD-7 | phenothiazine-NH-Ph(SO₂Ph)-CH(Ph)(CN), with o-CN on phenyl | |
| LAD-8 | phenothiazine-NH-Ph-CH(CN)(CN) | |
| LAD-9 | phenothiazine-NH-Ph(SO₂Ph)-CH(CN)(CN) | +0.70 |
| LAD-10 | phenothiazine-NH-Ph-CH(CO₂Et)(CN) | |
| LAD-11 | phenothiazine-NH-Ph(SO₂Ph)-CH(CO₂Et)(CN) | +0.65 |

TABLE 2-continued

| No. | Leuco Dye | $E_{ox}$ |
|---|---|---|
| LAD-12 | phenothiazine-NH-C6H3(S)-CH(CONH2)(CN) | +0.54 |
| LAD-13 | phenothiazine-NH-C6H2(SO2Ph)-CH(CONH2)(CN) | +0.69 |
| LAD-14 | phenothiazine-NH-C6H3-CH(CO-C6H5)(CN) | |
| LAD-15 | phenothiazine-NH-C6H2(SO2Ph)-CH(CO-C6H5)(CN) | |
| LAD-16 | phenothiazine-NH-C6H3-NH-C6H5 | +0.25 |
| LAD-17 | phenothiazine-NH-C6H2(SO2Ph)-NH-C6H5 | +0.29 |
| LAD-18 | phenothiazine-NH-C6H3-NH-C6H4-Cl | +0.25 |
| LAD-19 | phenothiazine-NH-C6H2(SO2Ph)-NH-C6H4-Cl | +0.35 |

TABLE 2-continued
| No. | Leuco Dye | $E_{ox}$ |
|---|---|---|
| LAD-20 | 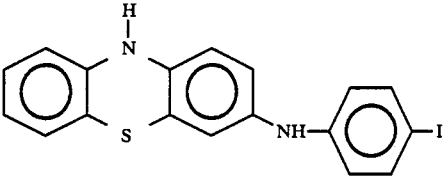 | +0.23 |
| LAD-21 | 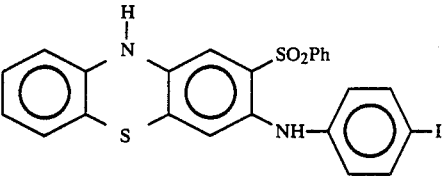 | +0.45 |
| LAD-22 | 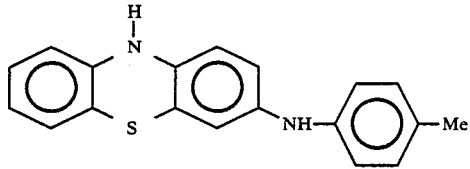 | |
| LAD-23 | 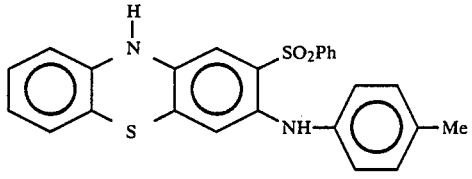 | +0.31 |
| LAD-24 | 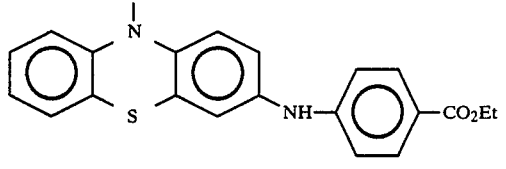 | +0.35 |
| LAD-25 | 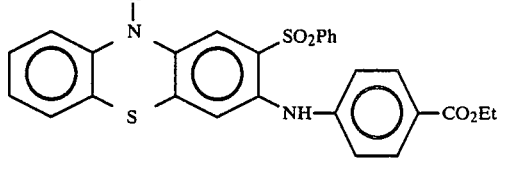 | |
| LAD-26 | 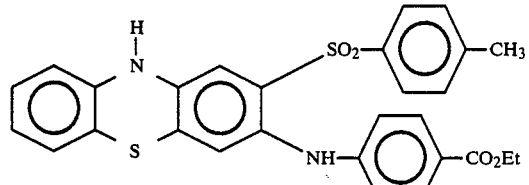 | |
| LAD-27 | 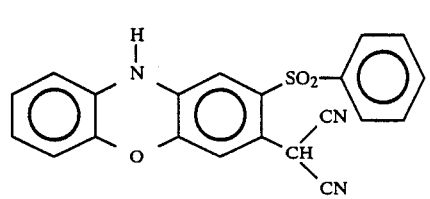 | |

TABLE 2-continued

| No. | Leuco Dye | $E_{ox}$ |
|---|---|---|
| LAD-28 | phenothiazine-NH linked to benzene with $SO_2$-C$_6$H$_4$-OMe, CN, CH-$CO_2Et$ | |
| LAD-29 | phenothiazine-NH linked to benzene with $SO_2$-C$_6$H$_4$-CH$_3$, CN, CH-$CO_2Et$ | |
| LAD-30 | phenothiazine-NH linked to benzene with $SO_2$-naphthyl, CN, CH-$CO_2Et$ | |
| LAD-31 | phenothiazine-NH linked to benzene with $SO_2$-C$_6$H$_4$-Cl, CN, CH-$CO_2Et$ | |
| LAD-32 | phenothiazine-NH linked to benzene with $SO_2$-C$_6$H$_4$-NO$_2$, CN, CH-$CO_2Et$ | |
| LAD-33 | phenothiazine-NH linked to benzene with $SO_2C_8F_{17}$, CN, CH-$CO_2Et$ | |

The invention will now be illustrated by the following Examples.

EXAMPLE 1

Preparation of Dicyanomethylene-3H-phenothiazine (Compound AD-3)

Finely powdered phenothiazine, 2 g (0.01 mole), was dissolved with stirring in 70 ml boiling methanol. Potassium acetate, 4 g, was added and the mixture cooled to 30° C. Malonitrile, 1 g (0.015 mole), was then added, followed by a solution of 3 g iodine in 70 ml methanol.

After stirring at room temperature for 1 hour, the precipitate was filtered and washed repeatedly with methanol. The dye was recrystallised from chloroform-methanol, to give a blue black powder, yield 1.1 g (42%).

EXAMPLE 2

Preparation of 3-(2,2-dimethyl-4,6-dioxo-1,3-dioxanylidene-(5'))-3H-phenoxazine (Compound AD-1)

The procedure of Example 1 was followed but using phenoxazine (0.47 g), potassium acetate (1.5 g), Meldrum's Acid (1 g) and iodine (1.3 g).

Brown purple leaflets were recrystallised from dimethylformamide-methanol at a yield of 0.4 g (50%).

NMR, δ(ppm): 1.85 (singlet, 6H), 7.1–8.8 (multiplet, 7H).

EXAMPLE 3

Preparation of 3-(3-phenyl-5-oxo-isoxazolylidene-(4))-3H-phenothiazine (Compound AD-11)

The procedure of Example 1 was followed, using 3-phenyl-5-isoxazolone instead of malononitrile.

EXAMPLE 4

Preparation of 3-(p-carbethoxyphenylimino)-3H-phenothiazine (Compound AD-14)

To a warm and stirred suspension of 4 g (0.02 mole) finely powdered phenothiazine and 4 g (0.024 mole) ethyl-p-aminobenzoate in 200 ml methanol was added a solution of 10 g of iodine in 150 ml methanol. After stirring at room temperature for 2 hours, the dark precipitate was filtered, washed repeatedly with methanol, and dissoved in 100 ml chloroform and 10 ml triethylamine. The chloroform solution was shaken with water and separated. Purification through alumina and recrystallisation from ether gave purple leaflets. Yield 5.5 g (76%).

NMR, δ(ppm) 1.4 (triplet, 3H), 4.33 (quartet, 2H), 6.5–8.5 (Multiplet, 11H, ArH).

EXAMPLE 5

Preparation of 3-(2,4-dimethoxyphenylimino)-3H-phenothiazine (Compound AD-20)

The procedure of Example 4 was followed, using 2,4-dimethoxyaniline instead of ethyl-p-aminobenzoate, to give purple leaflets, yield 49%.

EXAMPLE 6

Preparation of 7-trifluoromethyl-dicyanomethylene-3H-phenothiazine (Compound AD-28)

To a stirred solution of 2.6 g 7-trifluoromethylphenothiazine, 1 g malononitrile and 4 g potassium acetate in 70 ml methanol was added a solution of 4 g iodine in 50 ml methanol. The precipitated dye was filtered, washed repeatedly with methanol and recrystallised in chloroform-methanol. Yield 0.6 g (18%).

EXAMPLE 7

Preparation of 5-methyl-dicyanomethylene-3H-phenazine (Compound AD-29)

The procedure of Example 6 was followed but using N-methylphenazinium toluenesulphonate to give a blue dye. Yield 15%.

Additional data for the azine dyes of the Examples together with the other dyes of the invention are given in the following Table 3.

TABLE 3

| Dye | Calculated % by weight | | | Found % by weight | | | Melting Point °C. |
|---|---|---|---|---|---|---|---|
|  | C | H | N | C | H | N |  |
| AD-1 (Example 2) | 66.87 | 4.02 | 4.33 | 66.50 | 4.23 | 4.41 | >340 |
| AD-3 (Example 1) | 68.96 | 2.68 | 16.09 | 68.77 | 2.95 | 16.78 | 302 |
| AD-5 | 64.52 | 3.23 | 15.05 | 63.69 | 3.68 | 14.86 | 233–5 |
| AD-6 | 74.12 | 3.53 | 8.23 | 75.04 | 3.35 | 8.20 | 237–9 |
| AD-9 | 37.89 | 1.47 | 2.95 | 37.77 | 2.16 | 3.73 | 205–7 |
| AD-10 | 74.78 | 3.26 | 12.46 | 75.86 | 3.44 | 11.30 | 215–7 |
| AD-11 (Example 3) | 70.79 | 3.17 | 7.86 | 70.01 | 3.17 | 7.24 | 207–9 |
| AD-14 (Example 4) | 70.00 | 4.44 | 7.78 | 69.75 | 4.60 | 7.65 | 143–5 |
| AD-15 | 66.98 | 3.41 | 8.68 | 67.03 | 3.34 | 9.88 | 183–4 |
| AD-16 | 52.17 | 2.66 | 6.76 | 52.27 | 2.66 | 6.82 | 208–9 |
| AD-18 | 75.50 | 4.64 | 9.27 | 75.61 | 4.67 | 9.32 | 161–3 |
| AD-20 (Example 5) | 68.96 | 4.60 | 8.05 | 69.01 | 4.49 | 8.17 | 152–3 |
| AD-22 | 70.40 | 5.60 | 11.20 | 69.95 | 5.57 | 12.13 | 172–3 |
| AD-23 | 72.29 | 4.82 | 8.43 | 72.23 | 4.77 | 9.37 | 150–1 |
| AD-28 (Example 6) | 58.36 | 1.82 | 12.76 | 57.97 | 1.73 | 12.55 | — |
| AD-29 (Example 7) | 74.42 | 3.87 | 21.71 | 73.24 | 3.74 | 21.41 | — |

EXAMPLE 8

Preparation of 3-(4-carbethoxyanilino)-phenothiazine (Compound LAD-24)

To a stirred suspension of 1 g dye AD-14 in some warm acetone was added excess zinc dust and a few drops of concentrated HCl. The mixture was stirred until the colour discharged, and then filtered. The cake was extracted with hot acetone. The filtrate was combined, concentrated and poured into water. The precipitate was filtered, washed repeatedly with water and cold methanol and dried. Recrystallisation from methanol gave colourless powder which gradually turned pinkish upon contact with air. Yield 0.9 g (90%).

EXAMPLE 9

Preparation of 2-benzenesulphonyl-3-(4-carbethoxyanilino)-phenothiazine (Compound LAD-25)

To a warm, stirred solution of 1.8 g dye AD-14 in 50 ml tetrahydrofuran was added 0.8 g benzene sulphinic acid (obtained by adding sufficient dilute hydrochloric acid to an aqueous solution of benzene sulphinic acid sodium salt to cause precipitation of the free acid). After stirring for 1 hour at 40° C., the solvent was removed under vacuum. The yellowish solution was poured into water. The precipitate was filtered, washed repeatedly with distilled water and methanol. Recrystallisation from $CHCl_3$—methanol gave a yellowish powder. Yield 1.9 g (76%).

NMR, δ(ppm): 1.34 (triplet, 3H, $CH_3$), 4.3 (quartet, 2H, $CH_2$), 6.26 (singlet, 1H, NH), 6.8–8.0 (multiplet, 16H, ArH, NH).

EXAMPLE 10

Preparation of 3-carbamidocyanomethylphenothiazine (Compound LAD-12)

To a warm and stirred suspension of 2 g dye AD-5 in 50 ml N,N-dimethylformamide was added zinc dust and concentrated HCl until discolouration. The colourless solution was filtered and poured into water. The precipitate was filtered, washed repeatedly with distilled water and dried. Yellowish powder. Yield 1.8 g (90%).

EXAMPLE 11

(a) Preparation of 2-benzenesulphonyl-3-carbethoxycyanomethylphenothiazine (Compound LAD-11)

The procedure of Example 9 was followed, using AD-4 instead of dye AD-14, to give a yellowish powder.

(b) Preparation of compounds LAD-28 to LAD-33

Compounds LAD-28 to LAD-33 were prepared as for Compound LAD-11, but using the corresponding substituted sulphinic acid obtained in the following manner:

Preparation of p-chlorobenzenesulphinic acid sodium salt

To a stirred suspension of 12 g zinc dust in 300 ml boiling water was added portion-wise 21.1 g p-chlorobenzene-sulphonylchloride. After stirring 1 hour at 90° C., the mixture was cooled down and excess $Na_2CO_3$ added. The water was evaporated off leaving a mixture of white powder and zinc compound. The powder was repeatedly extracted with methanol and the extract was evaporated off. Acetone was then added and the precipitate was filtered, washed with acetone and dried. Yield 18 g.

The other sulphinic acids are similarly prepared.

Compounds LAD-28 to 33 were obtained in yields of 87.5%, 90%, 72%, 78% and 69% respectively.

Additional data for some leuco azine dyes of the Examples together with other leuco dyes of the invention are given in Table 4.

TABLE 4

| Leuco Dye | Calculated % by weight | | | Found % by weight | | | Melting Point °C. |
|---|---|---|---|---|---|---|---|
| | C | H | N | C | H | N | |
| LAD-8 | 68.44 | 3.42 | 15.97 | 67.56 | 3.53 | 15.69 | 201-3 |
| LAD-11 (Example 11) | 61.33 | 4.00 | 6.22 | 61.83 | 4.03 | 6.96 | 96-8 |
| LAD-12 (Example 10) | 64.06 | 3.91 | 14.95 | 63.80 | 4.02 | 14.69 | 176-8 |
| LAD-13 | 59.86 | 3.56 | 9.98 | 60.17 | 3.72 | 9.56 | 104-6 |
| LAD-18 | 66.56 | 4.01 | 8.63 | 66.39 | 4.03 | 8.31 | 173-4 |
| LAD-20 | 51.92 | 3.12 | 6.73 | 51.25 | 3.05 | 6.31 | 181-3 |
| LAD-24 (Example 8) | 69.61 | 4.97 | 7.73 | 69.47 | 5.43 | 8.19 | 172-4 |
| LAD-25 (Example 9) | 64.54 | 4.38 | 5.58 | 63.79 | 4.25 | 4.93 | 196-7 |
| LAD-29 | 62.07 | 4.31 | 6.03 | 62.66 | 3.98 | 6.86 | — |
| LAD-30 | 64.80 | 4.00 | 5.60 | 63.46 | 3.60 | 7.89 | — |

EXAMPLE 12

The use of a leuco dye in thermographic imaging

A solution of 0.1 g compound LAD-9, 1 g nickel nitrate and 10 g of a 15% Saran F-310 resin (a vinylidene chloride copolymer commercially available from Dow Chemical Company) in tetrahydrofuran was coated onto a polyester base using a K-bar coating rod, and air dried. The leuco dye coating was brought into contact with an original and subjected to infrared radiation in a transparency maker. A blue copy of the original was obtained.

EXAMPLE 13

The use of a leuco dye in pressure sensitive imaging

A paper impregnated wih a solution of compound LAD-18 was brought into contact with a paper coated with a dispersion of microencapsulated benzoyl peroxide. A purple image was generated by writing on the back of the leuco dye impregnated paper.

EXAMPLE 14

The use of leuco dyes in photothermographic imaging

A light sensitive silver behenate composition (dry silver) was prepared by mixing:

| | |
|---|---|
| silver behenate full soap homogenate | 14.1 g |
| toluene | 71.1 g |
| ethanol | 6.5 g |
| Butvar B-76 resin (polyvinylbutyral commercially available from Monsanto) | 7.5 g |
| zinc chloride solution (4.3 g zinc chloride in 100 ml ethanol) | 1 ml |

The composition was coated as 75 micron wet thickness onto Mylar film (polyethyleneterephthalate film commercially available from DuPont) and dried for 4 minutes at 85° C.

A topcoat composition utilising a leuco dye of the invention was then prepared by mixing:

| | |
|---|---|
| ethanol | 50 g |
| acetone | 42.5 g |
| Butvar B-76 resin | 7.5 g |
| UV-5411 ultraviolet absorber (2-(2'-hydroxy-5'-t-octylphenyl)benzotriazole commercially available from American Cyanamid) | 0.1 g |
| phthalic acid | 0.5 g |

0.05 g of a leuco dye of the invention was added to 8.0 g of this mixture and then mixed until the dye dissolved. This composition was then topcoated at 75 micron wet thickness onto a dry silver underlayer as described above and dried at 85° C. for 3 minutes.

The coatings were exposed to approximately $4.3 \times 10^4$ lux to obtain maximum image density (Dmax) and processed by heating at 127° C. for 3 seconds.

The leuco dyes of the invention which were used and the Dmax obtained are reported in the following table.

| Leuco Dye | Dmax |
|---|---|
| LAD 9 | 0.53 |
| LAD 12 | 1.70 |
| LAD 13 | 1.47 |
| LAD 18 | 1.63 |

I claim:

1. A compound of the general formula:

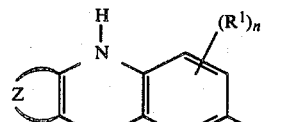

or $$\text{II}$$

(structure: fused ring system with N, X, Z, Q, and $(R^1)_n$ substituent)

in which:

X represents O or S;

Z represents the necessary atoms to complete a fused aromatic or heterocyclic ring system, which may be polynuclear, of up to 16 skeletal atoms selected from carbon and nitrogen;

n is 0 or 1;

$R^1$ represents an alkyl or aromatic sulphonyl group, containing up to 15 skeletal atoms selected from carbon, nitrogen, oxygen, and sulphur;

Q represents $CR^4R^5$ in which $R^4$ and $R^5$ each contain up to 20 skeletal atoms selected from carbon, nitrogen, oxygen and sulphur, at least one of $R^4$ and $R^5$ is selected from the group consisting of electronegative groups selected from the group consisting of carbonyl, cyano and sulphonyl groups, and substituted aryl groups, and the other of $R^4$ and $R^5$ may additionally be selected from aryl, alkoxy, thioalkoxy, alkylamino and arylamino, or $R^4$ and $R^5$ together comprise the necessary atoms to form a 5-membered α-oxoheterocyclic ring, and when X represents O, $R^4$ and $R^5$ together may additionally comprise the necessary atoms to form a 6-membered α-oxoheterocyclic ring.

2. A compound as claimed in claim 1, in which Z represents a fused phenyl ring or pyridine ring optionally substituted by a perfluoroalkyl group.

3. A compound as claimed in claim 1, in which $R^1$ is selected from an arylsulphonyl group optionally substituted by alkyl, alkoxy, halogen, nitro and a further fused ring, and a perfluoroalkylsulphonyl group.

4. A compound as claimed in any of claim 1, in which Q is $CR^4R^5$ and $R^4$ and $R^5$ are selected from carboxy, carboalkoxy, carboaryloxy, carbamido, arylaminocarbonyl, cyano, optionally perfluorinated alkylsulphonyl, arylsulphonyl, sulphamido, nitroaryl, cyanoaryl, alkanoyl, and aroyl or $R^4$ and $R^5$ together form a 5-membered α-oxoheterocyclic ring selected from oxazolidinone, thioxo oxazolidone, thiazolidone, thioxothiazolidone, oxazolone, thiazolone, pyrazolone, isoxazolone, isothiazolone, diazolidinedione and indanone, optionally substituted by one or more alkyl, aryl or fused ring groups.

5. A compound as claimed in any of claim 1, in which X represents O, and $R^4$ and $R^5$ together comprise the necessary atoms to form a 6-membered α-oxoheterocyclic ring selected from oxoisocoumarin and 1,3-dioxane-4,6-dione.

6. The compound of claim 1 wherein said at least one of $R^4$ and $R^5$ is an electronegative group selected from the group consisting of carbonyl, cyano and sulfonyl groups.

7. The compound of claim 2 wherein said at least one of $R^4$ and $R^5$ is an electronegative group selected from the group consisting of carbonyl, cyano and sulfonyl groups.

8. The compound of claim 3 wherein said at least one of $R^4$ and $R^5$ is an electronegative group selected from the group consisting of carbonyl, cyano and sulfonyl groups.

9. The compound of claim 4 wherein said at least one of $R^4$ and $R^5$ is an electronegative group selected from the group consisting of carbonyl, cyano and sulfonyl groups.

10. The compound of claim 5 wherein said at least one of $R^4$ and $R^5$ is an electronegative group selected from the group consisting of carbonyl, cyano and sulfonyl groups.

11. The compound of claim 1 wherein one of $R^4$ and $R^5$ is an aryl group.

12. The compound of claim 1 wherein said at least one of $R^4$ and $R^5$ is an aryl group having a substituent selected from the group consisting of alkyl, alkoxy and fused ring groups.

* * * * *